(12) United States Patent
Schönfeld

(10) Patent No.: US 7,204,834 B2
(45) Date of Patent: Apr. 17, 2007

(54) APPARATUS FOR THE TREATMENT OF TUMORS

(76) Inventor: Andreas Schönfeld, Im Schlehert 28, 78187 Karlsruhe (DE)

( * ) Notice: Subject to any disclaimer, the term of this patent is extended or adjusted under 35 U.S.C. 154(b) by 309 days.

(21) Appl. No.: 10/704,491

(22) Filed: Nov. 8, 2003

(65) Prior Publication Data

US 2004/0097918 A1    May 20, 2004

Related U.S. Application Data

(63) Continuation-in-part of application No. PCT/DE02/01178, filed on Mar. 30, 2002.

(30) Foreign Application Priority Data

May 30, 2001 (DE) .......................... 201 09 099 U

(51) Int. Cl.
*A61B 18/18* (2006.01)

(52) U.S. Cl. ...................................... 606/41

(58) Field of Classification Search ................. 606/32, 606/41–42, 45–50; 604/114
See application file for complete search history.

(56) References Cited

U.S. PATENT DOCUMENTS

| 4,188,927 | A | * | 2/1980 | Harris | 606/38 |
| 5,674,267 | A | * | 10/1997 | Mir et al. | 607/72 |
| 5,766,153 | A | * | 6/1998 | Eggers et al. | 604/114 |
| 5,888,198 | A | * | 3/1999 | Eggers et al. | 604/114 |
| 6,638,275 | B1 | * | 10/2003 | McGaffigan et al. | 606/41 |
| 6,712,840 | B2 | * | 3/2004 | Sun | 607/96 |
| 6,962,587 | B2 | * | 11/2005 | Johnson et al. | 606/41 |
| 2002/0120259 | A1 | * | 8/2002 | Lettice et al. | 606/32 |

* cited by examiner

*Primary Examiner*—Roy D. Gibson
*Assistant Examiner*—Pete Vrettakos
(74) *Attorney, Agent, or Firm*—Klaus J. Bach

(57) ABSTRACT

In apparatus for the treatment of tumors, comprising at least one generator having a power source, and at least two electrode needles for conducting current into, or out of, a tumor, a control arrangement is provided for limiting the current flowing through each electrode to a maximum value.

3 Claims, 1 Drawing Sheet

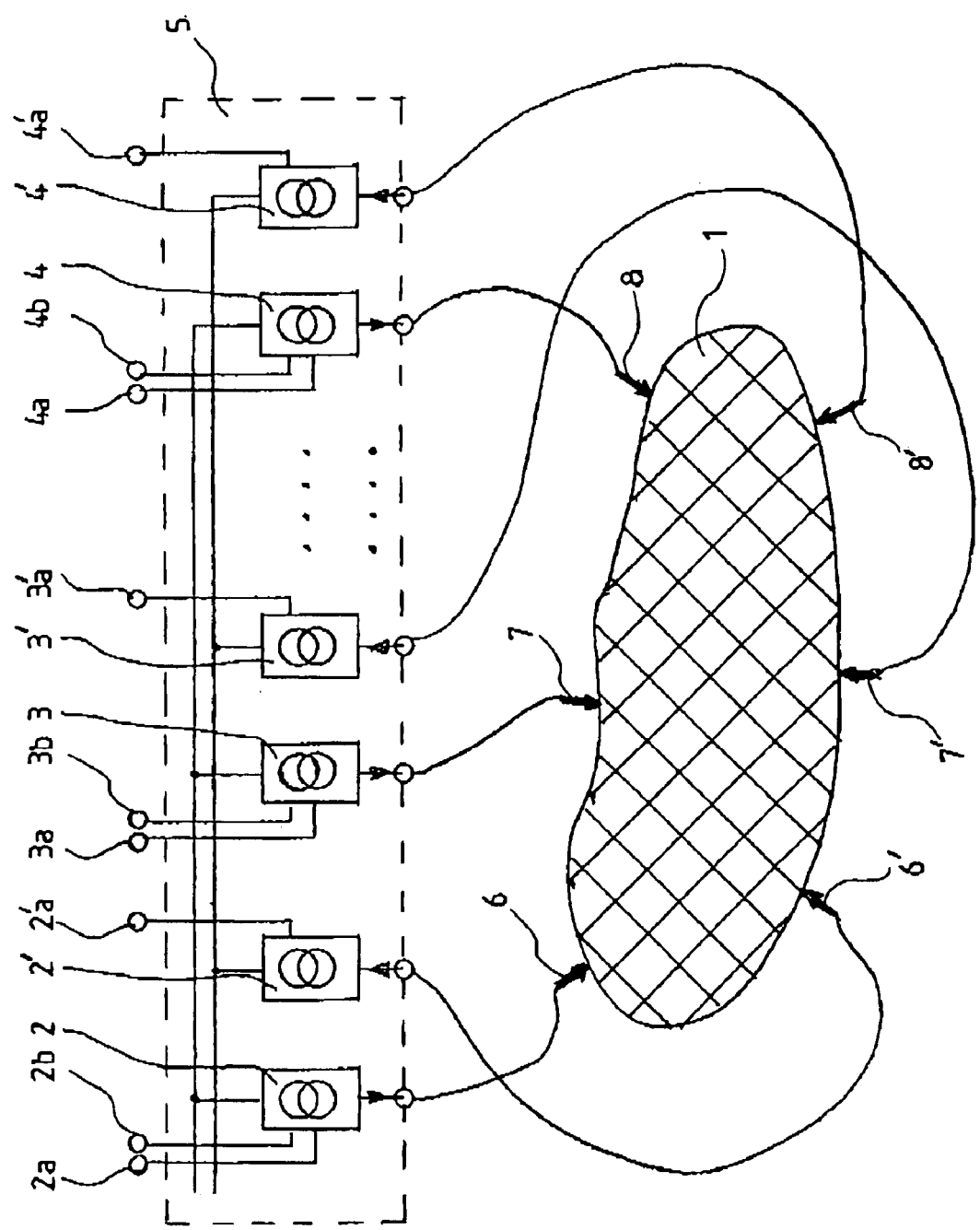

APPARATUS FOR THE TREATMENT OF TUMORS

This is is a Continuation-In-Part application of international application PCT/DE02/01178 filed Mar. 30, 2002 and claiming the priority of German application 201 09 099.6 filed May 30, 2001.

BACKGROUND OF THE INVENTION

The invention relates to an apparatus for the treatment of tumors, the apparatus comprising at least one generator having a power source, and at least two needle electrodes by means of which current can be conducted into, and out of, the tumor.

Such an apparatus is for instance known from the document "Percutaneous Bio-electrotherapy of Cancerous Tumors", Dr. Med. Rudolf Pekar, Publishing House Wilhelm Maudrich, Vienna-Munich-Berne, 1997. The apparatus disclosed therein comprises two needle-shaped electrodes, one for conducting current into the tumor and one for conducting current out of the tumor. By means of the apparatus known, direct current is conducted through a tumor. This is done by inserting the two needle-shaped electrodes into the tumor, and then applying a DC voltage to the electrodes, so that a direct current flows through the tumor. Such a current is intended to destroy cancerous cells in the tumor.

It has been found that the method is more efficient the more current is conducted through the tumor. Therefore a current is selected which is as high as possible. Since, however, it has also been found that the tissue around the insertion location of the needle-shaped electrode is undesirably damaged by a current of approximately 80 milliampere and more, the current cannot be increased arbitrarily with an apparatus having needle-shaped electrodes.

The apparatus known from the document mentioned comprises two systems with separate outputs. It would thus be conceivable to use both systems in a parallel treatment of one and the same tumor. The current conducted into the tumor might then actually be doubled, with the current conducted into the tumor by each of the electrodes being limited to a maximum value. Since, however, the current travels through the tumor in an uncontrolled manner, it is not guaranteed that the current will, in correspondence with its introduction, again be conducted out of the tumor via the respective pertinent electrode. There is rather the risk that, due to the inhomogenous electric conductivity of the tumor, the current will pass through the tumor in such a way that it predominantly exits via one electrode, and that merely a residual current is conducted out of the tumor via the other electrode. This would destroy the tissue around the needle-shaped electrode via which the major part of the current exits from the tumor. The document therefore does not indicate, either that the two systems may be used in parallel for the treatment of one tumor, but rather it is indicated that the two systems are provided for the treatment of two patients that is of two different tumors at a time.

It the principal an object of the invention to provide an apparatus for the treatment of tumors such that it is suited for the unproblematic treatment of tumors with relatively high currents.

SUMMARY OF THE INVENTION

In apparatus for the treatment of tumors, comprising at least one generator having a power source, and at least two electrode needles for conducting current into, or out of, a tumor, a control arrangement is provided for limiting the current flowing through each electrode to a maximum value.

The fact that a control means is available by means of which the respective current flowing through the electrodes can be limited to a maximum value advantageously provides that, at no electrode, more current is conducted into the tumor or, respectively, out of the tumor than is possible without causing damage to the tissue. Due to the control means, several electrodes may be used simultaneously.

Since the maximum current flowing through the electrodes is limited to a maximum value, it remains without consequences, if for instance an electrode is inserted into the tumor at a position that would, due to a high electric conductivity, be chosen as a preferred way out of the tumor by several current paths through the tumor, that is for currents emanating from different electrodes. By the limitation of the current flowing through any of the electrodes to a maximum value, the currents are forced to search for ways through the tumor to other electrodes.

A particular embodiment of the invention has turned out to be particularly advantageous, wherein each electrode is fed by a separate power source. This means that each electrode by means of which current is conducted into the tumor is connected to a separate power source. Likewise, each electrode, by means of which current is conducted out of the tumor, is connected to a power source or, in other words, to a current sink, with the direction of the current being reversed with respect to the power sources. By feeding the electrodes using different power sources and current sinks, respectively, the limitation of the current flowing through the electrodes to a maximum value can be put into practice in a simple manner.

It is of particular advantage when the power sources are designed as constant current power sources.

In another embodiment of the invention, the current supplied by the power sources is adjustable at least for those power sources by which current can be conducted into the tumor. Thus, it is possible in a simple manner to provide for current flows through the tumor, which are locally different. The current flow through the tumor may further be influenced by the fact that the currents taken up by the current sinks can also be adjusted. Irrespective of the adjustability of the currents emitted by the power source or the currents taken up by the current sinks, respectively, the currents to remain limited to a respective maximum value, this maximum value being the same for all power sources or current sinks, respectively.

Further details, features and advantages of the present invention will become more readily apparent from the following description of a particular embodiment with reference to the accompanying drawing:

BRIEF DESCRIPTION OF THE DRAWINGS

The sole FIGURE shows an embodiment of an apparatus according to the invention.

DESCRIPTION OF A PREFERRED EMBODIMENT

As shown in the FIGURE, a generator 5 comprises several power sources 2, 3, 4 and several corresponding current sinks 2', 3', 4'; the outputs of the power sources 2, 3, 4 are connected to electrode needles 6, 7, 8. The connectors of the current sinks 2', 3', 4' are connected to electrodes needles 6', 7', 8'. The electrode needles 6, 6', 7, 7' 8, 8' are inserted into the tissue of a tumor 1.

The power sources 2, 3, 4 each comprise a control input 2*a*, 3*a*, 4*a* by means of which the maximum value of the current supplied by the respective power source can be adjusted. Furthermore, the power sources 2, 3, 4 each comprises a further control input 2*b*, 3*b*, 4*b* by means of which the current provided by the respective power source can be controlled. The current sinks 2', 3', 4' comprise, similar to the power sources 2, 3, 4, a control input 2'*a*, 3'*a*, 4'*a* by means of which the maximum value of the respective current taken up by the current sinks can be controlled.

If the power sources 2, 3, 4 are adjusted such that they each provide a current of, for instance, 80 milliampere, and if the current sinks 2', 3', 4' are adjusted such that the current maximally taken up by each of them is, for instance, limited to 80 milliamperes, the tumor 1 can be treated with 240 milliampere without the risk of the tissue being damaged at the position of insertion of an electrode. Even if, for instance, the electric conductivity of the tumor 1 were such that a part of the current which is conducted into the tumor 1 by means of the electrode 7 would flow to the electrode 6', and the current conducted into the tumor 1 by the electrode 6 would completely flow to the electrode 6', the limitation of the maximum current of the current sink 2' to 80 milliampere would prevent that the corresponding part of the current conducted into the tumor 1 by means of the electrode 7 will be conducted out of the tumor 1 via the electrode 6'. The current will therefore have to find a way to another electrode, that is, to the electrode 7'.

The invention is of course not limited to the arrangement as shown in the FIGURE. Although the FIGURE only illustrates three power sources and three current sinks, a much higher number of power sources and current sinks can be used. This is indicated by the dotted lines 17 shown in the FIGURE.

What is claimed is:

1. An apparatus for the treatment of tumors (1), comprising at least one generator (5) having at least one power source (2, 3, 4), at least one power sink (2', 3', 4'), at least one electrode input needle (6, 7, 8) connected to a power source (2, 3, 4) and at least one electrode output needle (6', 7', 8') connected to a power sink (2', 3', 4') by means of which current can be conducted into, or, respectively, out of, the tumor (1), a separate power supply control means (2*a*, 3*a*, 4*a*) connected to each power source (2, 3, 4) for independently controlling the current flowing through each input electrode needle (6, 7, 8) into the tumor (1) and, a separate power sink control means (2'*a*, 3'*a*, 4'*a*) connected to each power sink (2', 3', 4') for independently limiting the current flowing through each output electrode needle (6', 7', 8') out of the tumor (1).

2. An apparatus according to claim 1, wherein said power sources and sinks (2, 2', 3, 3', 4, 4') are constant current power sources.

3. An apparatus according to claim 1, wherein the current control means provided for the power sources and, respectively, sinks (2, 2', 3, 3', 4, 4') are adjustable.

* * * * *